United States Patent
Kim et al.

(10) Patent No.: US 9,915,623 B2
(45) Date of Patent: Mar. 13, 2018

(54) OPTICAL INSPECTION APPARATUS, A METHOD OF INSPECTING A SUBSTRATE, AND A METHOD OF TREATING A SUBSTRATE

(71) Applicant: Samsung Electronics Co., Ltd., Suwon-si, Gyeonggi-do (KR)

(72) Inventors: Kwang Soo Kim, Pyeongtaek-si (KR); Taejoong Kim, Hwaseong-si (KR); Byeonghwan Jeon, Yongin-si (KR); Yongsuk Choi, Hwaseong-si (KR); Youngduk Kim, Seongnam-si (KR); Taeseok Oh, Suwon-si (KR); SangYun Lee, Suwon-si (KR); Yong-Ho Choi, Hwaseong-si (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 15/218,584

(22) Filed: Jul. 25, 2016

(65) Prior Publication Data

US 2017/0082552 A1 Mar. 23, 2017

(30) Foreign Application Priority Data

Sep. 23, 2015 (KR) .......................... 10-2015-0134702

(51) Int. Cl.
*G01N 21/00* (2006.01)
*G01N 21/95* (2006.01)
(Continued)

(52) U.S. Cl.
CPC ... *G01N 21/9501* (2013.01); *G01N 21/95623* (2013.01); *G02B 3/0006* (2013.01); *G02B 13/0095* (2013.01); *G02B 27/0988* (2013.01)

(58) Field of Classification Search
CPC ......... G01N 21/9501; G01N 21/95623; G01N 21/95607; G01N 21/88; G01N 21/95;
(Continued)

(56) References Cited

U.S. PATENT DOCUMENTS

| 5,719,405 A | 2/1998 | Hayano |
| 7,345,825 B2 | 3/2008 | Chuang et al. |

(Continued)

FOREIGN PATENT DOCUMENTS

| JP | 2011169743 | 3/2011 |
| JP | 2014044134 | 3/2014 |

*Primary Examiner* — Jamil Ahmed
(74) *Attorney, Agent, or Firm* — Myers Bigel, P.A.

(57) ABSTRACT

An optical inspection apparatus includes an inspection target unit on which an inspection target is loaded, an illumination optical unit configured to irradiate incident light to the inspection target, an objective lens unit disposed between the illumination optical unit and the inspection target unit, a detection optical unit configured to receive reflective light reflected from the inspection target to thereby detect a presence or absence of a defect on the inspection target, and a control unit configured to control the illumination optical unit and the detection optical unit. The illumination optical unit includes a light source part configured to irradiate the incident light, and a spatial filter array configured to modify a transmission region of the incident light irradiated from the light source part. The spatial filter array includes a spatial filter part, and a filter movement part configured to move the spatial filter part.

17 Claims, 11 Drawing Sheets

(51) Int. Cl.
*G02B 27/09* (2006.01)
*G02B 13/00* (2006.01)
*G02B 3/00* (2006.01)
*G01N 21/956* (2006.01)

(58) Field of Classification Search
CPC .. G01N 23/00; G02B 3/0006; G02B 13/0095; G02B 27/0988; G02B 21/0016; G02B 23/18; G02B 21/26; G02B 3/00; A61B 6/032; A61B 6/00; H04N 5/335; H04N 5/222

See application file for complete search history.

(56) References Cited

U.S. PATENT DOCUMENTS

| | | | |
|---|---|---|---|
| 7,359,044 B2 | 4/2008 | Nishiyama et al. | |
| 8,294,125 B2 | 10/2012 | Han et al. | |
| 8,867,020 B2 | 10/2014 | Smilde et al. | |
| 2002/0097831 A1* | 7/2002 | Cheng | A61B 6/032 378/20 |
| 2007/0058164 A1* | 3/2007 | Shibata | G01N 21/95607 356/237.2 |
| 2007/0206279 A1* | 9/2007 | Brueck | G02B 21/0016 359/391 |
| 2010/0182475 A1* | 7/2010 | Witte | G02B 23/18 348/308 |
| 2014/0185044 A1 | 4/2014 | Ishikawa et al. | |
| 2015/0131087 A1 | 5/2015 | Ohtsubo et al. | |

* cited by examiner

OPTICAL INSPECTION APPARATUS, A METHOD OF INSPECTING A SUBSTRATE, AND A METHOD OF TREATING A SUBSTRATE

CROSS-REFERENCE TO RELATED APPLICATION

This application claims priority to Korean Patent Application No. 10-2015-0134702, filed on Sep. 23, 2015, the disclosure of which is hereby incorporated by reference in its entirety.

BACKGROUND

The inventive concepts relate to an optical inspection apparatus and, more particularly, to an optical inspection apparatus capable of inspecting a defect on a substrate, a method of inspecting a substrate, and a method of treating a substrate.

As patterns included in a semiconductor device become finer and are complicated, it may be necessary to inspect a defect of the semiconductor device. Reliability and a process yield of the semiconductor device may be improved by inspecting any defects of the semiconductor device. Defects of the semiconductor device may be optically inspected.

SUMMARY

Embodiments of the inventive concepts may provide an optical inspection apparatus capable of improving inspection ability.

In an aspect, an optical inspection apparatus may include an inspection target unit on which an inspection target is loaded, an illumination optical unit configured to irradiate incident light to the inspection target, an objective lens unit disposed between the illumination optical unit and the inspection target unit, a detection optical unit configured to receive reflective light reflected from the inspection target to thereby detect a presence or absence of a defect exists on the inspection target, and a control unit configured to control the illumination optical unit and the detection optical unit. The illumination optical unit may include a light source part configured to irradiate the incident light, and a spatial filter array configured to modify a transmission region of the incident light irradiated from the light source part. The spatial filter array may include a spatial filter part, and a filter movement part configured to move the spatial filter part.

In some embodiments, the filter movement part may include a first filter movement part configured to move the spatial filter part in a first direction, and a second filter movement part configured to move the spatial filter part in a second direction perpendicular to the first direction.

In some embodiments, the spatial filter part may include a reference filter, and a processing filter having an opening designed using the reference filter.

In some embodiments, the reference filter may include a light shielding portion, and a hole surrounded by the light shielding portion. The control unit may be configured to control the illumination optical unit such that the opening is designed according to a result of a scanning process performed while moving the hole in at least one of the first direction or the second direction.

In some embodiments, the control unit may be configured to obtain defect data while performing the scanning process using the hole when the incident light is irradiated. The control unit may be configured to control positions of the hole corresponding to excess regions in which a signal-to-noise ratio of the defect data is higher than a critical value previously determined. The control unit may be configured to control the illumination optical unit and the detection optical unit such that a shape of the opening is designed based on the checked positions of the hole.

In some embodiments, the control unit is configured to control the illumination optical unit and the detection optical unit such that the scanning process is performed a plurality of times and such that the opening is designed using an average value extracted from the checked positions of the hole of the scanning processes performed the plurality of times.

In some embodiments, the optical inspection apparatus may be a bright field optical system.

In some embodiments, the detection optical unit may include a tube lens array. The tube lens array may include a first tube lens having a first magnification, and a second tube lens having a second magnification.

In some embodiments, the first magnification may be lower than the second magnification. The first tube lens may be configured to align the inspection target, and the second tube lens may be configured to detect a presence or absence of the defect exists on the inspection target.

In some embodiments, the detection optical unit may further include a second spatial filter disposed between the tube lens array and the objective lens unit. The second spatial filter may have a second opening having the same shape as the opening of the processing filter.

In some embodiments, the objective lens unit may include an objective lens, and a protective fluid supply part that supplies a protective fluid to a space between the objective lens and the inspection target.

In some embodiments, the protective fluid supply part may be disposed outside the objective lens.

In some embodiments, the objective lens unit may further include an objective lens cover surrounding the objective lens. The protective fluid supply part may be disposed to penetrate the objective lens cover.

In some embodiments, protective fluid supply part may be disposed in a body of the objective lens.

In an aspect, a method of inspecting a substrate may include irradiating incident light to a substrate, disposing a spatial filter on an optical path of the incident light, revising a transmission region of the incident light using the spatial filter, and extracting reflective light reflected from the substrate to detect a presence or absence of a defect on the substrate or. The revising of the transmission region may include disposing a hole restricting the transmission region of the incident light on the optical path, obtaining defect data according to a position of the hole while moving the hole, and designing an opening of the spatial filter, which defines a shape to be modified of the transmission region, based on the defect data.

In some embodiments, the obtaining of the defect data and the designing of the opening may include performing a scanning process while moving the hole, obtaining the defect data according to the position of the hole, comparing the defect data, checking positions of the hole corresponding to excess regions in which a signal-to-noise ratio of the defect data is higher than a critical value, and designing the opening based on the checked positions of the hole.

In some embodiments, the method includes performing the scanning process a plurality of times. In this case, the designing of the opening may further include extracting an average value of defect data obtained by the scanning processes performed the plurality of times. The checking of the positions of the hole may include checking the positions of the hole based on the average value.

In some embodiments, the extracting of reflective light to detect whether the defect exists on the substrate may include selecting a tube lens from tube lenses having different magnifications from each other that has an aberration optimized according to a magnification of the reflective light.

In an aspect, a method of inspecting a substrate may include performing a first process on a first substrate, irradiating incident light to the first substrate, on which the first process is performed, through a first spatial filter having a first opening configured to modify a transmission region of the incident light, extracting reflective light reflected from the first substrate to detect a presence or absence of a first defect on the first substrate, performing a second process on a substrate, irradiating the incident light to the second substrate, on which the second process is performed, through a second spatial filter having a second opening configured to modify the transmission region of the incident light, and extracting reflective light reflected from the second substrate to detect a presence or absence of a second defect on the second substrate. Each of the first and second openings may be designed using a hole restricting the transmission region of the incident light, and the first and second openings may have shapes that are different from each other.

In some embodiments, each of the first and second openings may be designed by performing a scanning process while moving the hole restricting the transmission region of the incident light on an optical path of the incident light, obtaining defect data according to a position of the hole, checking positions of the hole corresponding to excess regions in which a signal-to-noise ratio of the defect data is higher than a critical value, and designing each of the first and second openings based on the checked positions of the hole.

In some embodiments, the first substrate may be the same as the second substrate.

In some embodiments, the first process may be the same as the second process.

In some embodiments, the first defect may be the same as the second defect.

In an aspect, a method of treating a substrate may include performing a treating process on a substrate, irradiating incident light to the substrate on which the treating process is completed, revising a transmission region of the incident light using a spatial filter, and receiving reflective light reflected from the substrate to perform an inspection process inspecting a presence or absence of a defect on the substrate. A shape of an opening of the spatial filter used in the inspection process may be designed differently according to a type of the treating process.

In some embodiments, the shape of the opening may be designed by performing a scanning process while moving a hole, obtaining defect data according to a position of the hole, comparing the defect data, checking positions of the hole corresponding to excess regions in which a signal-to-noise ratio of the defect data is higher than a critical value, and designing the opening based on the checked positions of the hole.

In some embodiments, method includes performing the scanning process a plurality of times.

In an aspect, an illumination optical unit for an optical inspection apparatus including an inspection target unit on which an inspection target is loaded; an illumination optical unit configured to irradiate incident light to the inspection target; an objective lens unit disposed between the illumination optical unit and the inspection target unit; and a control unit configured to control the illumination optical unit and the detection optical unit is provided. The illumination optical unit comprises a light source part configured to irradiate the incident light; and a spatial filter array comprising: a spatial filter part configured to modify a transmission region of the incident light irradiated from the light source part; and a filter movement part configured to move the spatial filter part.

In some embodiments, the filter movement part comprises: a first filter movement part configured to move the spatial filter part in a first direction; and a second filter movement part configured to move the spatial filter part in a second direction perpendicular to the first direction.

In some embodiments, the spatial filter part comprises: a reference filter; and a processing filter having an opening designed using the reference filter.

In some embodiments, the reference filter comprises: a light shielding portion; and a hole surrounded by the light shielding portion, wherein the control unit is configured to control the illumination optical unit such that the opening is designed according to a result of a scanning process performed while moving the hole in at least one of the first direction or the second direction.

In some embodiments, the reference filter comprises a plurality of reference filters.

BRIEF DESCRIPTION OF THE DRAWINGS

The inventive concepts will become more apparent in view of the attached drawings and accompanying detailed description.

DETAILED DESCRIPTION OF THE EMBODIMENTS

Figure 1:
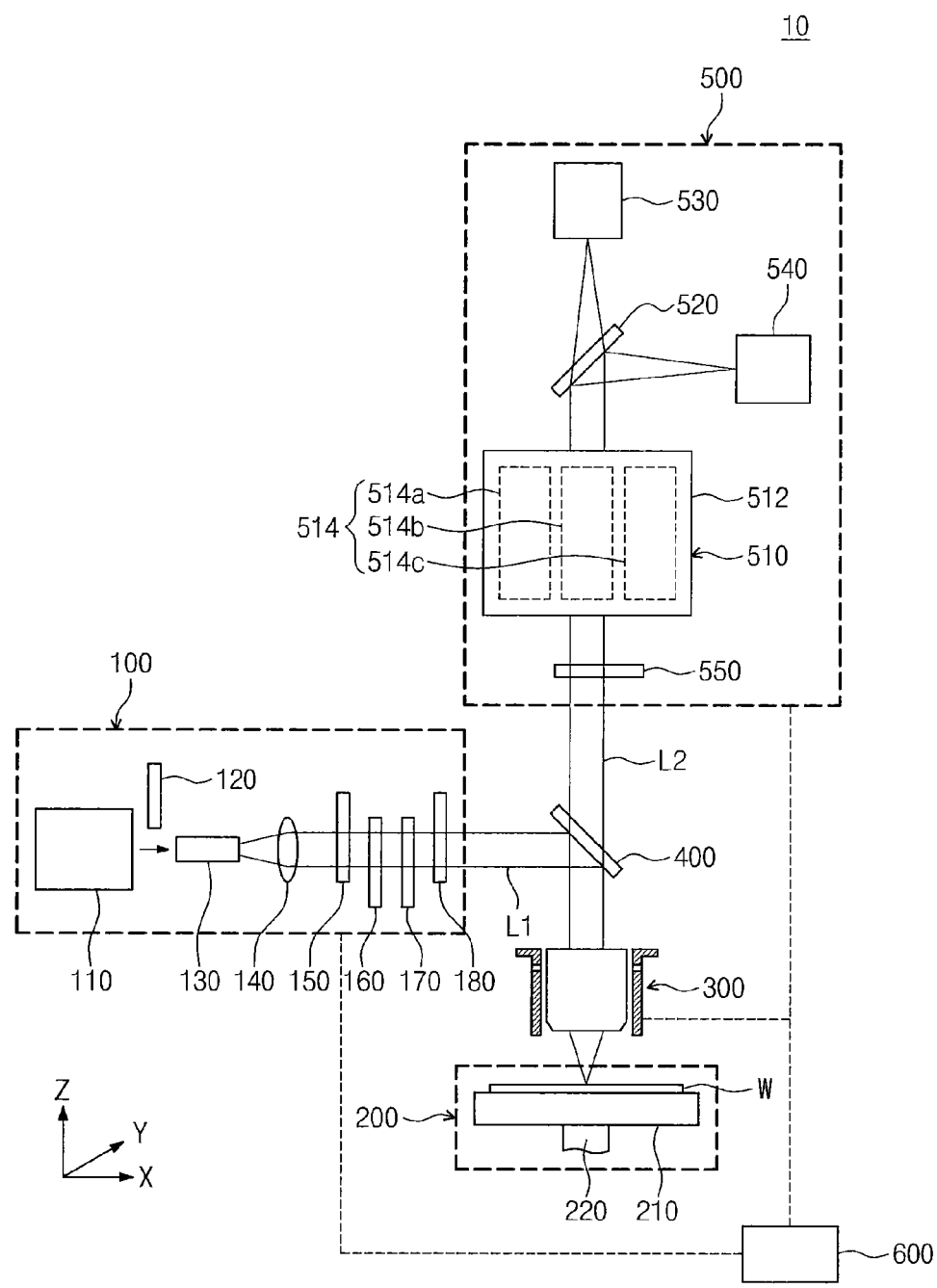
FIG. 1 is a schematic view illustrating an optical inspection apparatus according to some embodiments of the inventive concepts.

The inventive concepts will now be described more fully hereinafter with reference to the accompanying drawings, in which exemplary embodiments of the inventive concepts are shown. The inventive concepts and methods of achieving them will be apparent from the following exemplary embodiments that will be described in more detail with reference to the accompanying drawings. The embodiments of the inventive concept may, however, be embodied in different forms and should not be constructed as limited to the embodiments set forth herein. Rather, these embodiments are provided so that this disclosure will be thorough and complete, and will fully convey the scope of the inventive concept to those skilled in the art.

As used herein, the singular terms "a," "an" and "the" are intended to include the plural forms as well, unless the context clearly indicates otherwise. It will be understood that when an element is referred to as being "connected" or "coupled" to another element, it may be directly connected or coupled to the other element or intervening elements may be present. As used herein, the term "and/or" includes any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Exemplary embodiments of aspects of the present inventive concepts explained and illustrated herein include their complementary counterparts. The same reference numerals or the same reference designators denote the same elements throughout the specification.

FIG. 1 is a schematic view illustrating an optical inspection apparatus 10 according to some embodiments of the inventive concepts. Referring to FIG. 1, the optical inspection apparatus 10 may include an illumination optical unit 100, an inspection target unit 200, an objective lens unit 300, a first beam splitter 400, a detection optical unit 500, and a control unit 600. The optical inspection apparatus 10 may inspect whether a defect occurs on an inspection target or not. In some embodiments, the inspection target may be a semiconductor substrate (e.g., a wafer), and the defect may include a foreign substance (e.g., a particle) or abnormal growth of a pattern. Hereinafter, the inspection target corresponding to a wafer W will be described as an example. In certain embodiments, the inspection target may be a glass substrate or another kind of a semiconductor device. In some embodiments, the optical inspection apparatus 10 may be a bright field optical system.

The illumination optical unit 100 may include a light source part 110, a shutter 120, a rod lens 130, a collimating lens 140, a spatial filter array 150, a spectral filter 160, a polarizing filter 170, and a neutral density (ND) filter 180. The light source part 110 may generate and irradiate incident light L1. In some embodiments, the light source part 110 may be, but not limited to, laser produced plasma (LPP). The incident light L1 may have a short wavelength. For example, the incident light L1 may have a wavelength of about 100 nm to about 300 nm. The shutter 120 may be provided in front of the light source part 110. The shutter 120, the rod lens 130, the collimating lens 140, the spatial filter array 150, the spectral filter 160, the polarizing filter 170, and the ND filter 180 may be disposed on an optical path of the incident light L1 irradiated from the light source part 110. The shutter 120 may be movable. The shutter 120 may be moved to block or open the light source part 110. Thus, the shutter 120 may control whether the incident light L1 of the light source part 110 is provided or not.

The rod lens 130 may be disposed such that its longitudinal direction is parallel to the optical path. The incident light L1 may be incident on an incident surface of the rod lens 130 and may be transmitted an output surface of the rod lens 130. The incident surface and the output surface may have the same shape and may have a regular polygon. The rod lens 130 may make the incident light L1 into uniform light. In some embodiments, a fly-eye lens may be provided instead of the rod lens 130. The collimating lens 140 may be provided in front of the rod lens 130. The incident light L1 transmitted from the rod lens 130 may be condensed while passing through the collimating lens 140. Thus, the incident light L1 may be converted from a diverging beam into a collimated beam.

Figure 2A:
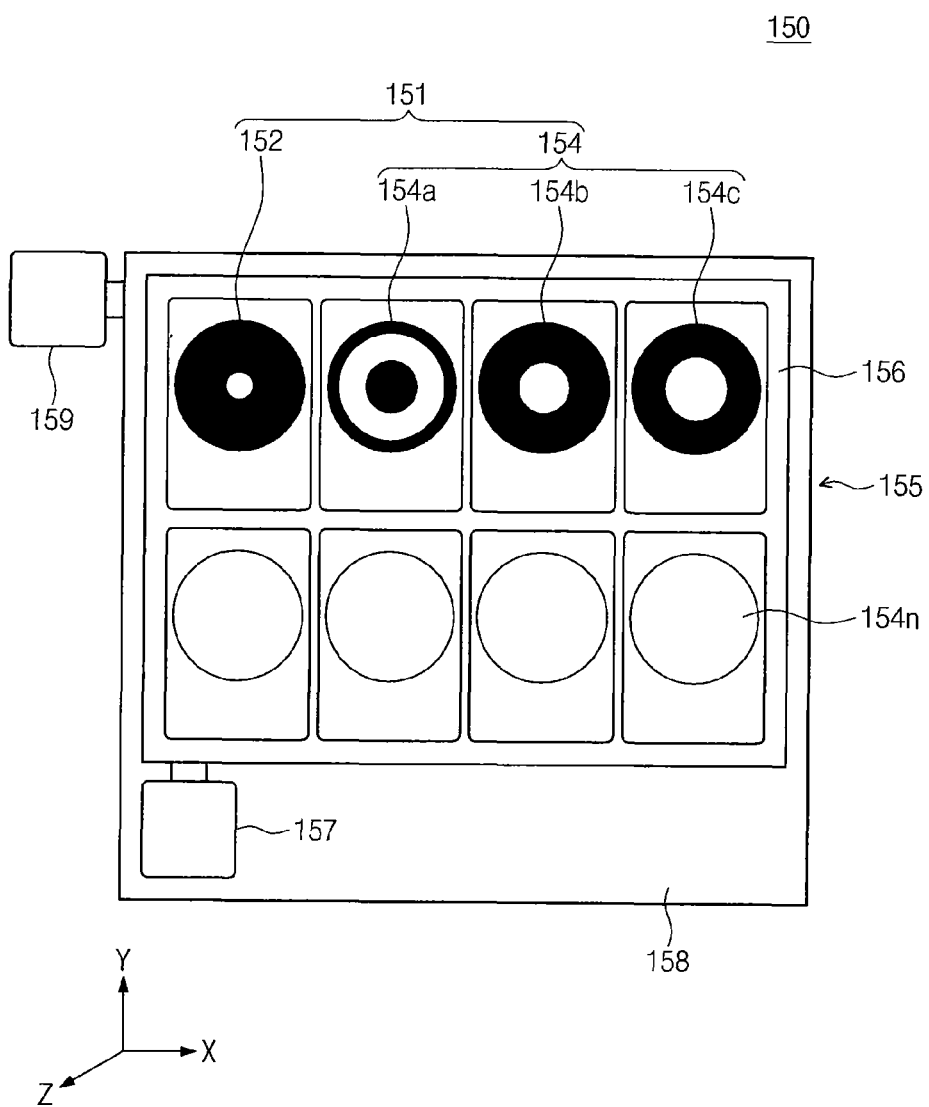
FIG. 2A is a schematic view illustrating a spatial filter array.
Figure 2B:
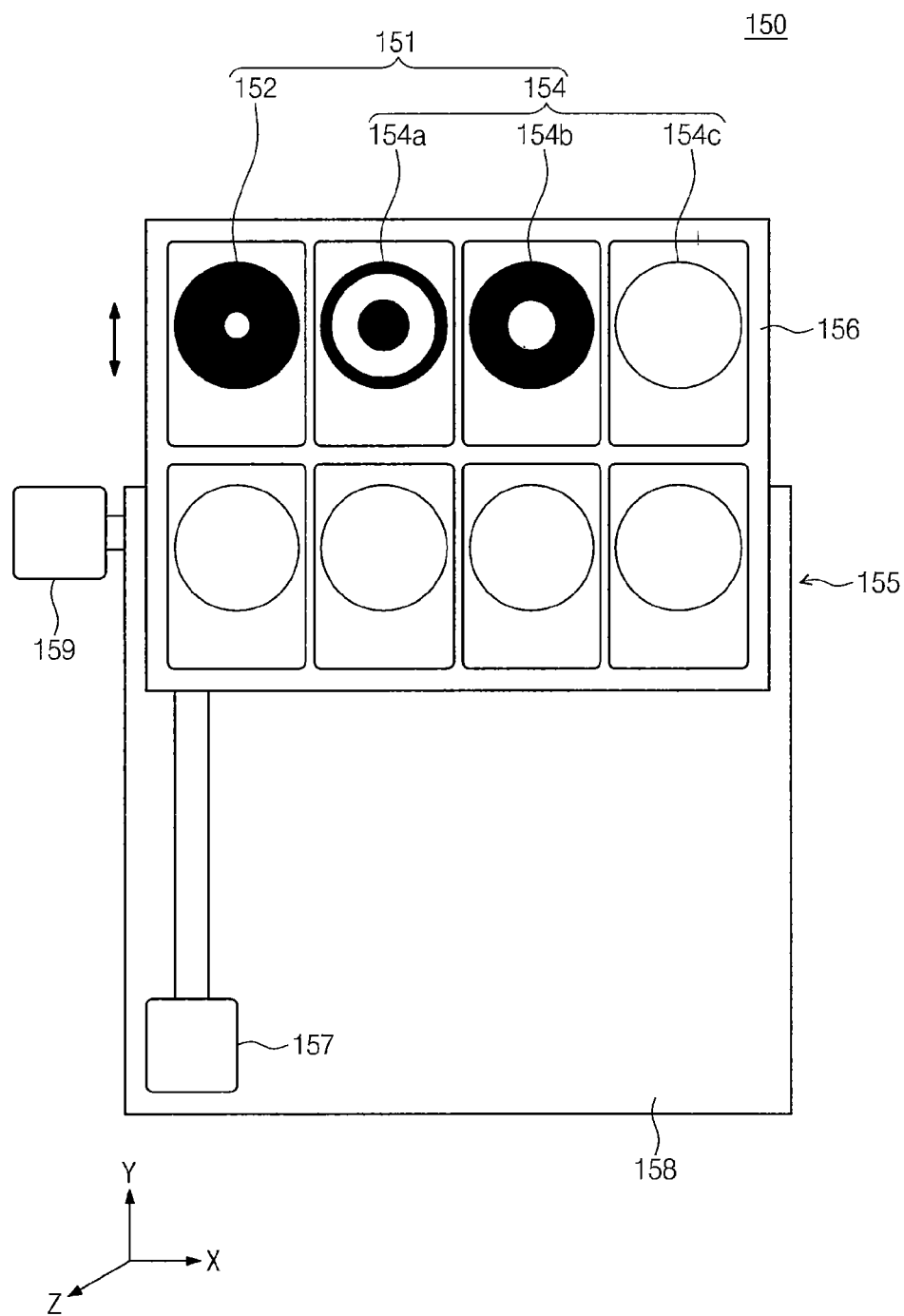
FIG. 2B is a schematic view illustrating an operation of moving a spatial filter part by a filter movement part.

FIG. 2A is a schematic view illustrating a spatial filter array. FIG. 2B is a schematic view illustrating an operation of moving a spatial filter part by a filter movement part. Referring to FIGS. 2A and 2B, the spatial filter array 150 may include a spatial filter part 151 and a filter movement part 155. The spatial filter part 151 may spatially control the incident light L1 such that the incident light L1 may pass through a portion of an irradiation region IR of FIG. 3B. In other words, the spatial filter part 151 may modify a transmission region of the incident light L1. The spatial filter part 151 may include a reference filter 152 and a processing filter 154. In FIGS. 2A and 2B, a dark portion of each of the filters 152 and 154 refers to a light shielding portion, and a bright portion of each of the filters 152 and 154 refers to an opening defining a transmission region IR' of FIG. 3B through which the incident light L1 is transmitted. As illustrated in FIGS. 2A and 2B, the openings respectively included in the filters 152 and 154 may have different shapes, different positions and/or different sizes from each other.

Figure 3A:
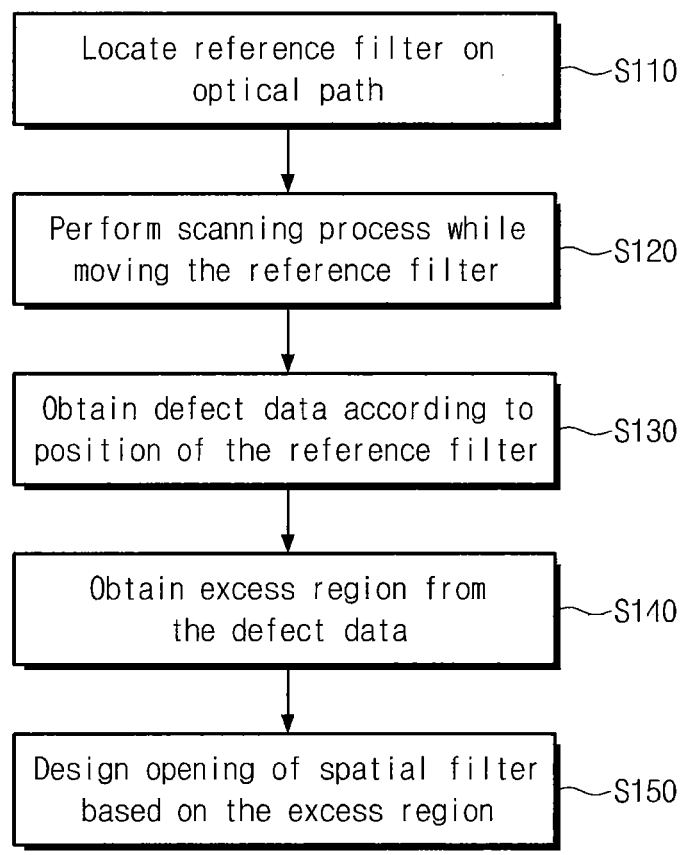
FIG. 3A is a flow chart illustrating a method of designing a processing filter using a reference filter.
Figure 3B:
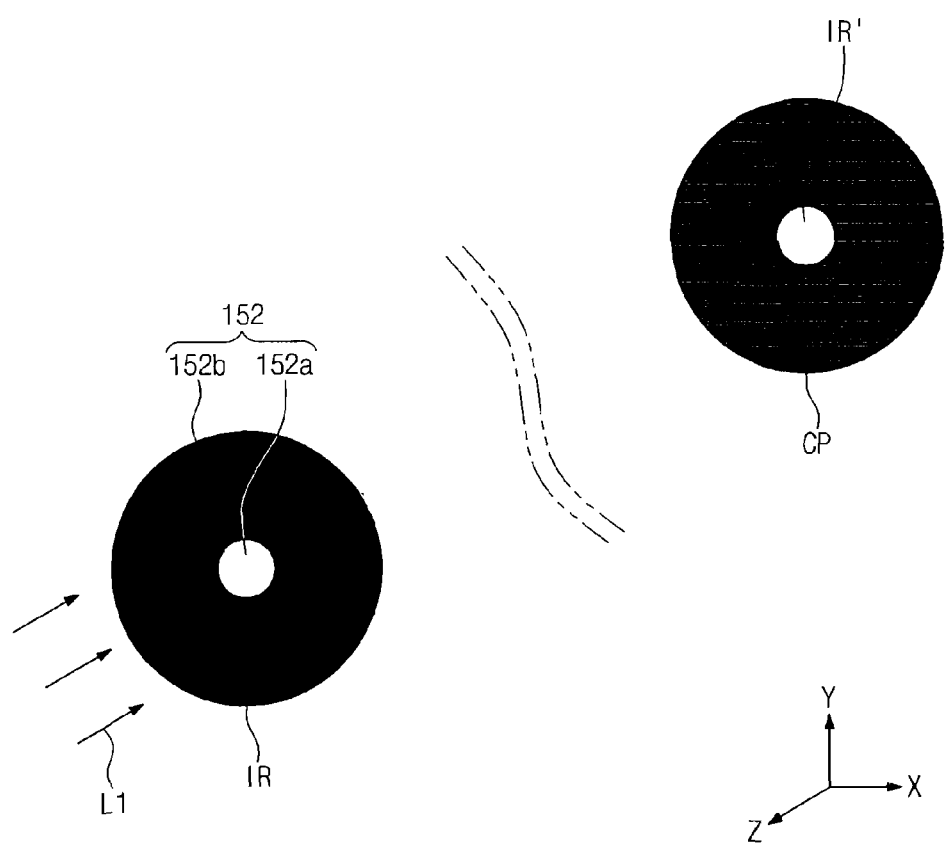
FIGS. 3B to 3H are schematic views illustrating a method of designing a processing filter using a reference filter.
Figure 3C:
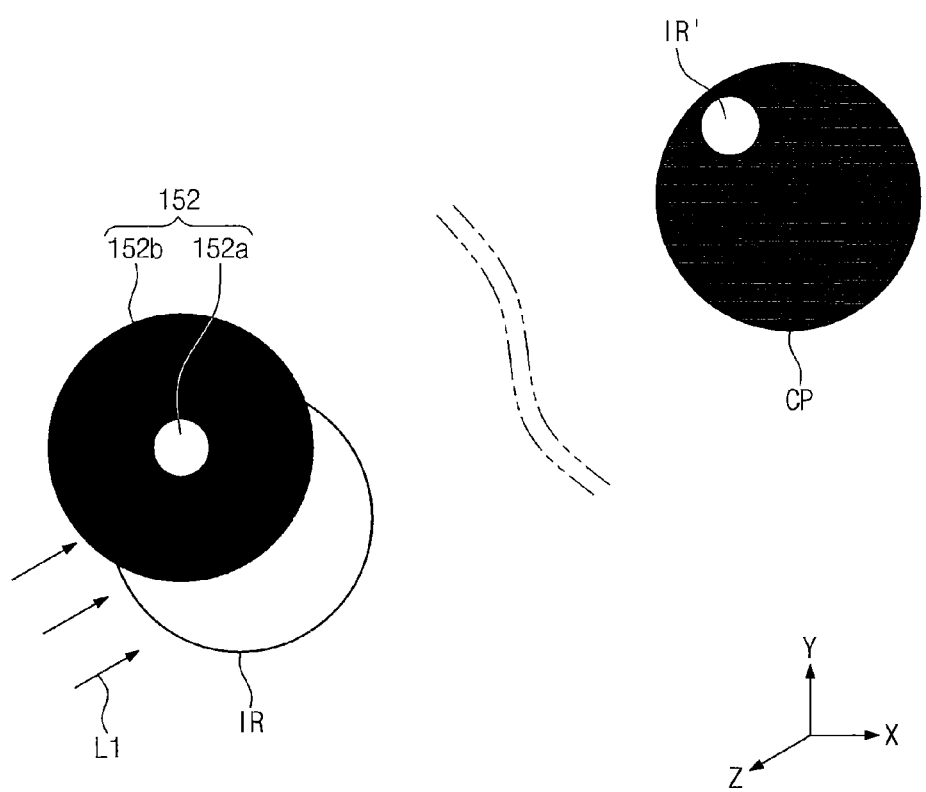
Figure 3D:
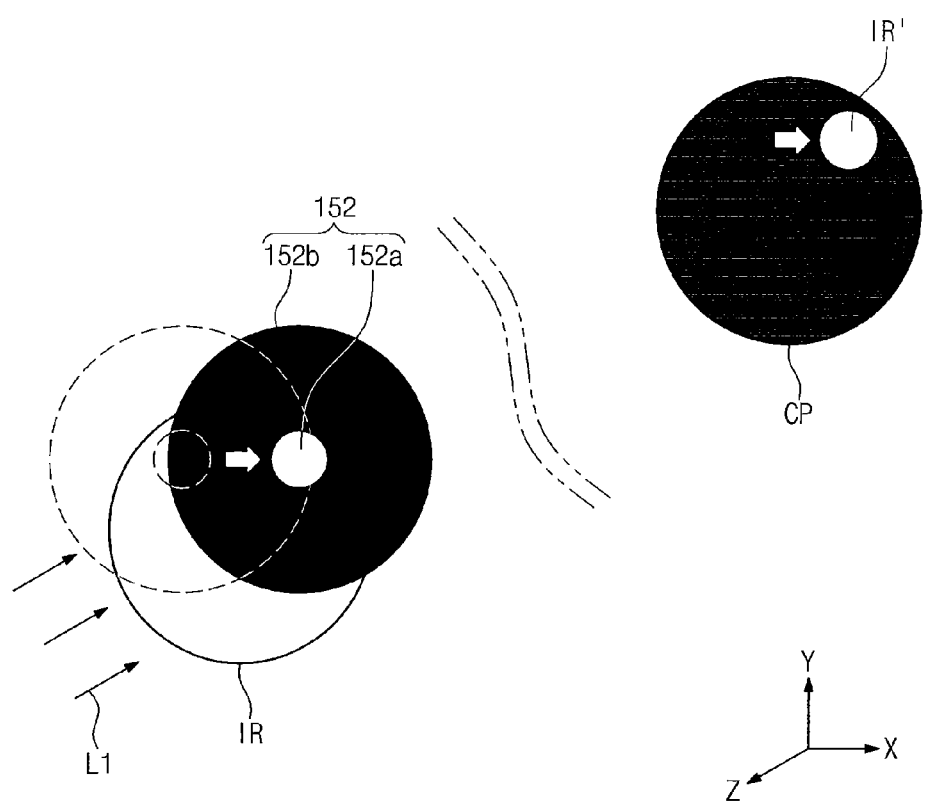
Figure 3E:
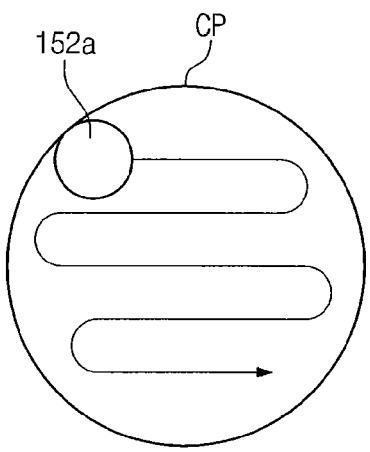

The reference filter 152 may include a reference opening 152a of FIG. 3B and a reference light shielding portion 152b of FIG. 3B. The reference opening 152a may define the transmission region IR' of the incident light L1 illustrated in FIG. 3B. The reference opening 152a may be formed in a central portion of the reference filter 152 and may have a small-sized hole shape. Hereinafter, the reference opening 152a may be referred to interchangeably as a reference hole 152a for the purpose of ease and convenience in explanation. The reference light shielding portion 152b may surround the reference hole 152a. The reference filter 152 may be formed of a quartz material, and the reference light shielding portion 152b may be formed by plating the reference filter 152 with a specific material. For example, the reference light shielding portion 152b may be formed by plating the reference filter 152 with chrome (Cr). An entire portion of the reference filter 152 may be exposed, but the transmission region IR' of the incident L1 may be determined according to the size, the shape and/or the position of the reference hole 152a.

In some embodiments, the processing filter 154 may be provided by a plurality of processing filters. In some embodiments, the processing filter 154 may include a first processing filter 154a, a second processing filter 154b, a third processing filter 154c, . . . , and an n-th processing filter 154n. The first processing filter 154a may have the same shape, size, and material as the reference filter 152. The first processing filter 154a may include a first opening 154aa of FIG. 3G and first light shielding portions 154ab and 154ac of FIG. 3G. At this time, a shape, a position and a size of the first opening 154aa may be different from those of the reference opening 152a, and shapes, positions and sizes of the first light shielding portions 154ab and 154ac may be different from those of the reference light shielding portion 152b. Likewise, as illustrated in FIGS. 2A and 2B, the processing filters 154a, 154b, 154c, . . . , and 154n may have the same shape, the same size, and the same material, but openings and light shielding portions of the processing filters 154a, 154b, 154c, . . . , and 154n may have different shapes, different positions and different sizes from each other.

Each of the processing filters 154a, 154b, 154c, . . . , and 154n having different openings and different light shielding portions from each other may be designed using the reference filter 152. In other word, each of the processing filters 154a, 154b, 154c, . . . , and 154n may be designed to define transmission regions IR' of the incident light L1, which are different from each other. The control unit 600 may select one of the processing filters 154a, 154b, 154c, . . . , and 154n to perform an inspection process, as occasion arises. Thus, the optical inspection apparatus 10 may select a processing filter optimized according to a kind of a defect, a kind of a recipe, a kind of the inspection target, and/or a kind of a material of the inspection target, thereby performing the inspection process. As a result, inspection ability and reliability of the inspection process may be improved.

FIG. 3A is a flow chart illustrating a method of designing the processing filter 154 using the reference filter 152. FIGS. 3B to 3H are schematic views illustrating a method of designing the processing filter 154 using the reference filter 152. FIGS. 3B to 3H are illustrated using an equivalent model for the purpose of ease and convention in explanation and views. Hereinafter, a method of designing the first processing filter 154a using the reference filter 152 will be described as an example. The irradiation region IR may correspond to a region on which the incident light L1 is incident. In addition, the irradiation region IR may correspond to a plane in which the spatial filter part 151 is positioned. A pupil plane CP is a plane optically conjugated with the irradiation region IR. In some embodiments, the pupil plane CP may be an imaginary region in an objective lens 310. In other word, an image corresponding to the reference filter 152 of the irradiation region IR may be formed on the pupil plane CP.

Referring to FIGS. 3A and 3B, the reference filter 152 may be located on the path of the incident light L1 (S110). The reference filter 152 may be located on the irradiation region IR in which the incident light L1 is irradiated. The incident light L1 incident on the reference filter 152 does not pass through the reference light shielding portion 152b. Thus, the incident light L1 may pass through only the reference hole 152a and may pass through a pupil hole IR' of the pupil plane CP corresponding to the reference hole 152a. The pupil hole IR' may correspond to the transmission region IR'. Even though the incident light L1 passes through the pupil hole IR', the incident light L1 may diverge from the objective lens 310 to the inspection target W to reach an entire region of the inspection target W. Thus, the inspection process of detecting a defect may be performed on the entire region of the inspection target W, and the transmission region of the incident light L1 to the inspection target W may be controlled.

Referring to FIGS. 3A and 3C to 3E, a scanning process may be performed while moving the reference filter 152 (S120). The reference filter 152 may be moved by the filter movement part 155 along at least one of a first direction X or a second direction Y. In some embodiments, the reference filter 152 may be moved in a zigzag form. Thus, a position of the transmission region IR' of the incident light L1 transmitted through the reference hole 152a of the reference filter 152 may be changed. The detection optical unit 500 may detect a defect on the inspection target W corresponding to each of the positions of the reference hole 152a. In other word, the detection optical unit 500 may obtain defect data according to the position of the transmission region IR' of the incident light L1 (S130).

Figure 3F:
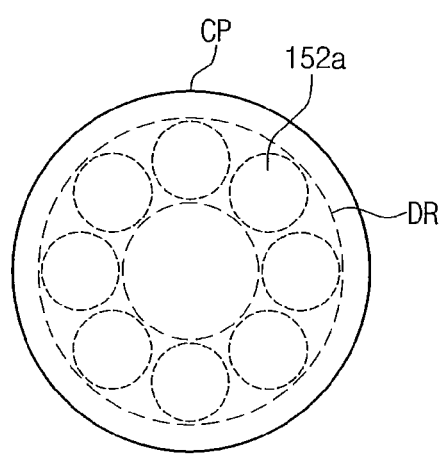
Figure 3G:
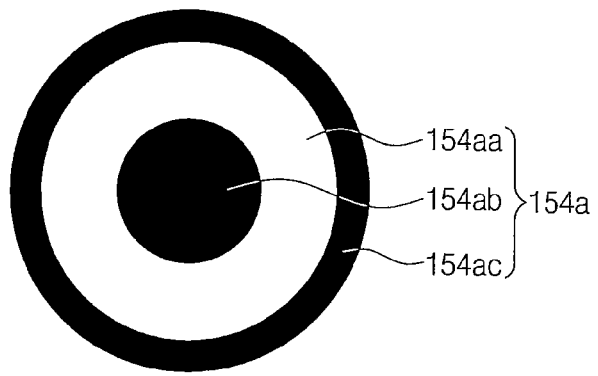

Referring to FIGS. 3A, 3F, and 3G, the control unit 600 may set a design region DR of the opening of the processing filter 154 on the basis of the defect data according to the position of the reference hole 152a. In other word, the control unit 600 may compare and analyze the defect data according to the position of the reference hole 152a to extract excess regions in which a signal-to-noise ratio (SNR) is higher than a predetermined critical value (S140). The control unit 600 may set the design region DR of the opening based on the excess regions. For example, the control unit 600 may set the design region DR of the opening based on shapes of the excess regions (S150). Referring to FIGS. 3F and 3G, the first opening 154aa and the first light shielding portions 154ab and 154ac of the first processing filter 154a may be set based on the design region DR.

Figure 3H:
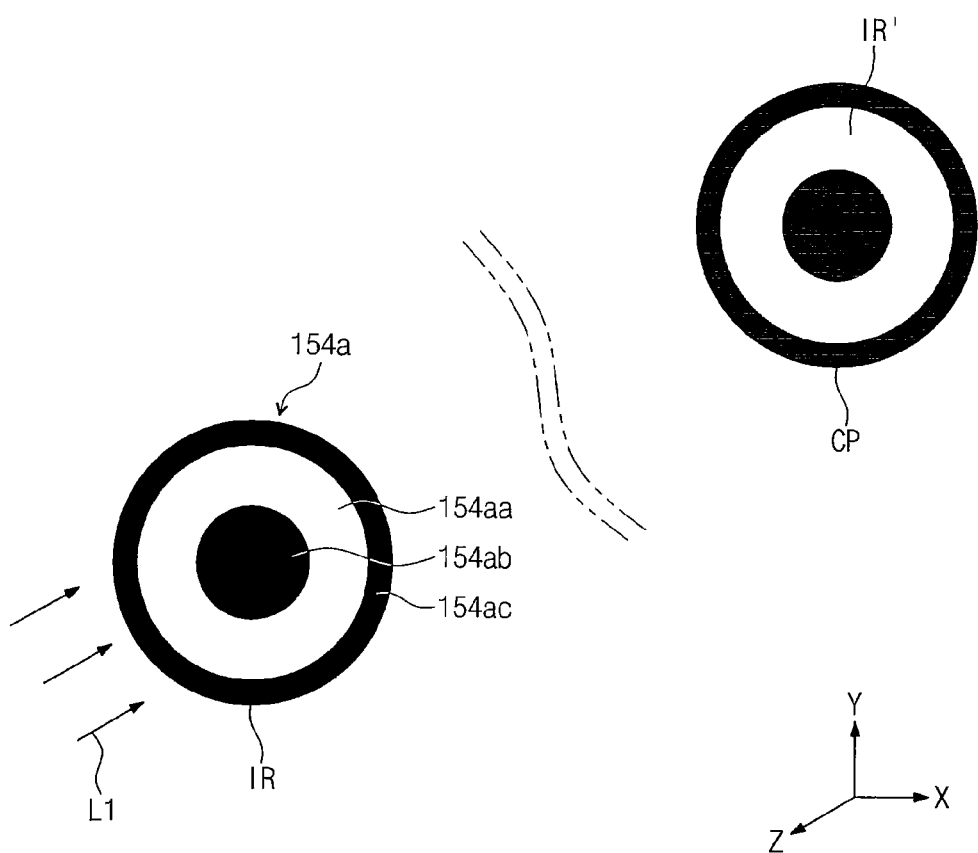

Referring to FIGS. 3A and 3H, the inspection process may be performed using the first processing filter 154a designed by the reference filter 152. The incident light L1 may be transmitted through the first opening 154aa of the first processing filter 154a. The incident light L1 corresponding to only the transmission region IR' of the pupil plane CP can be transmitted. Since the inspection process is performed selectively using only the incident light L1 of the region having a high SNR, the inspection ability and reliability of the inspection process may be improved.

FIGS. 3B to 3H illustrate the method of designing the first processing filter 154a using the reference filter 152. Likewise, the second to the n-th processing filters 154b to 154n may be designed using the reference filter 152 by the same method as the first processing filter 154a. The excess regions in which the SNR is higher than the critical value may be changed according to a type of the inspection target W, a type of recipe of a process performed on the inspection target, and a type of the defect. Thus, it is possible to design the processing filter 154 having the opening optimized to each inspection process.

Referring again to FIGS. 2A and 2B, the filter movement part 155 may include a frame 156, a first filter movement part 157, a plate 158, and a second filter movement part 159. The frame 156 may support the reference filter 152 and the processing filters 154a to 154n. In some embodiments, the frame 156 may support edges of the reference filter 152 and the processing filters 154a to 154n. The first filter movement part 157 may be coupled to one side of the frame 156. The first filter movement part 157 may move the frame 156 in the second direction Y. Thus, the reference filter 152 and the processing filters 154a to 154n may be moved along the second direction Y. The first filter movement part 157 may be coupled to the plate 158. The first filter movement part 157 may include a motor. The second filter movement part 159 may be coupled to one side of the plate 158. The second filter movement part 159 may move the plate 158 in the first direction X perpendicular to the second direction Y. Thus, the reference filter 152 and the processing filters 154a to 154n may be moved along the first direction X. The second filter movement part 159 may include a motor. The filter movement part 150 may move the reference filter 152 and the processing filters 154a to 154n on a focal plane of the collimating lens 140.

Referring again to FIG. 1, the spectral filter 160 may filter incident light having a specific wavelength. The polarizing filter 170 may control a polarization condition of the incident light. The ND filter 180 may control the brightness of the incident light. In other word, the filters 160, 170, and 180 may be provided to set an illumination condition suitable to a process environment. The filters 160, 170, and 180 may be replaceable. In some embodiments, one or some of the filters 160, 170, and 180 may be omitted.

The inspection target unit 200 may include a stage 210 and a stage movement part 220. The inspection target W may be loaded on the stage 210. The stage movement part 220 may move the stage 210. The stage movement part 220 may move the stage 210 in a third direction Z perpendicular to the first and second directions X and Y. Even though not shown in the drawings, the stage movement part 220 may receive focus data from a focus control part (not shown) and may move the stage 210 to adjust a height of the inspection target W on the basis of the received focus data. In some embodiments, the stage movement part 220 may move the stage 210 in at least one of the first direction X or the second direction Y.

Figure 4A:
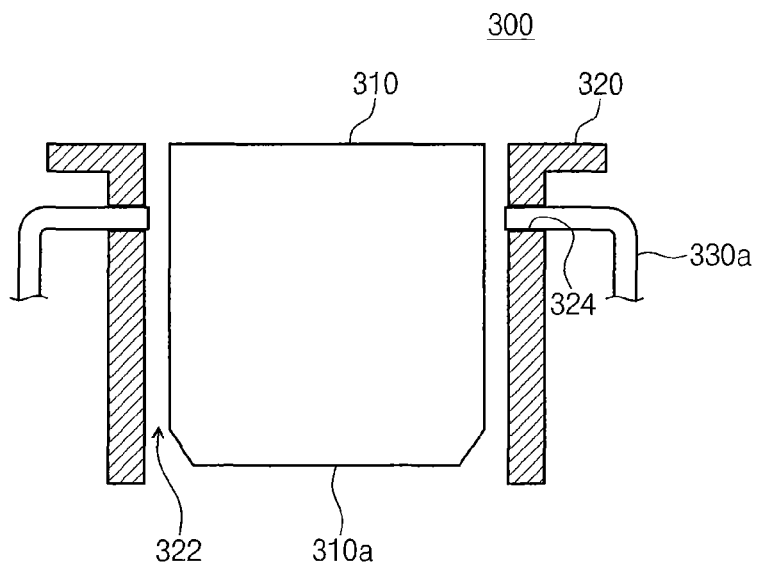
FIG. 4A is a schematic view illustrating a protective fluid supply part of an objective lens unit.
Figure 4B:
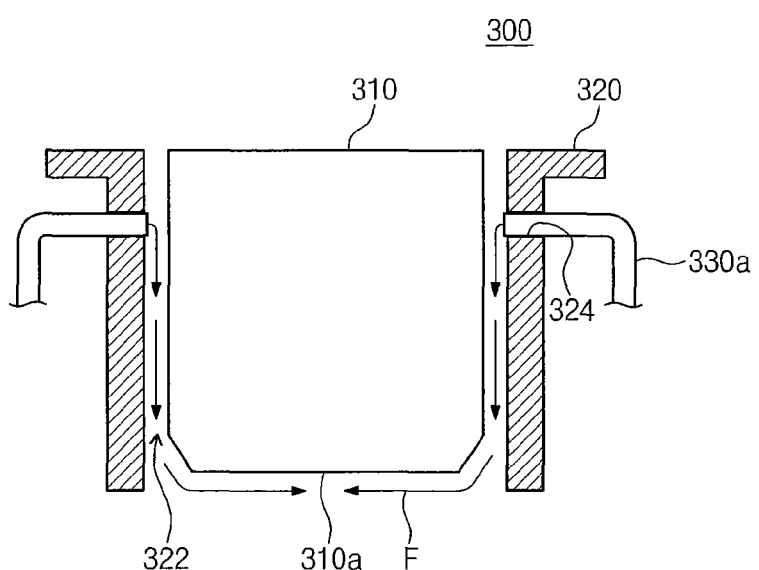
FIG. 4B is a schematic view illustrating an operation of supplying a protective fluid by the protective fluid supply part of FIG. 4A.
Figure 4C:
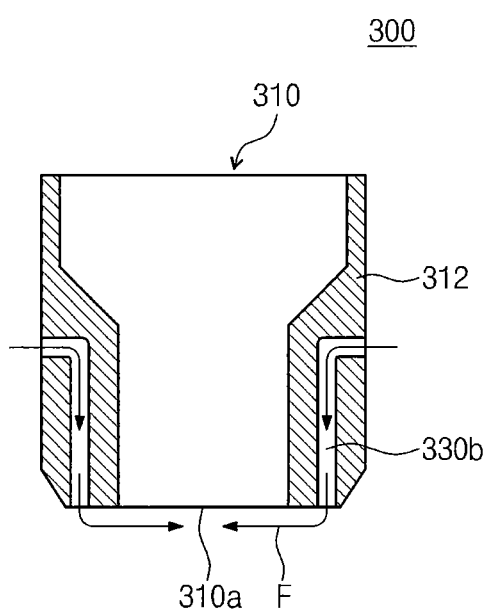
FIG. 4C is a schematic view illustrating a protective fluid supply part according to some embodiments of the inventive concepts.

FIG. 4A is a schematic view illustrating a protective fluid supply part 330a of the objective lens unit 300. FIG. 4B is a schematic view illustrating an operation of supplying a protective fluid by the protective fluid supply part 330a of FIG. 4A. FIG. 4C is a schematic view illustrating a protective fluid supply part 330b according to some embodiments of the inventive concepts. The objective lens unit 300 may include the objective lens 310, an objective lens cover 320, and the protective fluid supply part 330a. The objective lens 310 may condense the incident light L1 and may then irradiate the condensed light to the inspection target W. The objective lens cover 320 may be positioned exterior to the objective lens 310. The objective lens cover 320 may be spaced apart from the objective lens 310 by a specific distance and may surround the objective lens 310. Thus, the objective lens cover 320 may define a protective region 322. In other word, the protective region 322 may be defined between the objective lens cover 320 and the objective lens 310. A lower portion of the objective lens cover 320 may extend downward such that a bottom surface of the objective lens cover 320 may be lower than a bottom surface 310a of the objective lens 310. Thus, the objective lens cover 320 may prevent the objective lens 310 from colliding with an external component (e.g., a lift pin (not shown) protruding from the stage 210). Even though not shown in the drawings, a portion of an inner sidewall of the objective lens cover 320 may be coupled to a portion of an outer sidewall of the objective lens 310.

The protective fluid supply part 330a may supply a protective fluid F onto the bottom surface 310a of the objective lens 310. The protective fluid supply part 330a may supply the protective fluid F through the inside or the outside of the objective lens 310. As illustrated in FIG. 4B, the protective fluid supply part 330a may be provided through a through-hole 324 of the objective lens cover 320 to supply the protective fluid F. The protective fluid F may include a nitrogen ($N_2$) gas. When the incident light L1 is ultraviolet having a short wavelength (e.g., UVC), oxygen ($O_2$) may be converted into ozone ($O_3$). In general, ozone may be adsorbed on a surface of the objective lens 310 to form a thin film, and thus a transmittance of the objective lens 310 may be reduced and a reflectance of the objective lens 310 may be increased. Thus, a spot may occur on a detected image. In particular, the inside of the objective lens 310 may be protected by a nitrogen gas, but an exposed outer surface of the objective lens 310 may be affected by the ozone. In particular, the bottom surface 310a of the objective lens 310 facing the inspection target W may be weaker. Thus, the protective fluid F may be supplied to protect the objective lens 310 from ozone. Alternatively, as illustrated in FIG. 4C, a protective fluid supply part 330b may be disposed in a body 312 of the objective lens 310 to supply the protective fluid F.

The first beam splitter 400 may be provided on an optical path between the illumination optical unit 100 and the inspection target unit 200. The first beam splitter 400 may reflect a portion of light and may transmit another portion of the light. In other word, the first beam splitter 400 may reflect the incident light L1 irradiated from the illumination optical unit 100 to supply the reflected incident light to the objective lens unit 300 and may transmit reflective light L2 which is reflected from the inspection target W and then passes through the objective lens unit 300. In some embodiments, the first beam splitter 400 may include a half mirror.

Referring again to FIG. 1, the detection optical unit 500 may include a tube lens array 510, a second beam splitter 520, a first detector 530, and a second detector 540. The tube lens array 510 may include a body 512 and a tube lens part 514. The tube lens part 514 may be provided in the body 512. The tube lens part 514 may include a plurality of tube lenses. As illustrated in FIG. 1, the tube lens part 514 may include a first tube lens 514a, a second tube lens 514b, and a third tube lens 514c. The first, second, and third tube lenses 514a, 514b, and 514c may have magnifications different from each other. Since the first to third tube lenses 514a, 514b, and 514c may have magnifications different from each other, the control unit 600 may select an optimized one of the first to third tube lenses 514a, 514b, and 514c as the magnification is changed. Thus, the quality of an image detected by the detection optical unit 500 may be improved as compared with the quality of an image detected by an apparatus having a single focusing lens. In other word, one of the tube lenses of which each has the minimum aberration in a corresponding magnification may be selected to improve the quality of the detected image.

In some embodiments, the magnification of the first tube lens 514a may be lower than those of the second and third tube lenses 514b and 514c. In this case, the inspection target W may be aligned or observed using the first tube lens 514a, and a defect of the inspection target W may be detected using one of the second and third tube lenses 514b and 514c. In other word, when the tube lens part 514 includes the plurality of the tube lenses 514a to 514c, one or some thereof may be used to align the inspection target W and another or others thereof may be used to detect a defect of the inspection target W. In FIG. 1, three tube lenses 514a to 514c are illustrated as an example. However, embodiments of the inventive concepts are not limited thereto and any suitable number of tube lenses may be used.

The second beam splitter 520 may be disposed in front of the tube lens array 510. The second beam splitter 520 may guide the reflective light L2 to the first and second detectors 530 and 540. For example, the second beam splitter 520 may transmit a portion of the reflective light L2 to provide the transmitted portion of the reflective light L2 to the first detector 530 and may reflect another portion of the reflective light L2 to provide the reflected portion of the reflective light L2 to the second detector 540. In some embodiments, the second beam splitter 520 may include a half mirror.

The first detector 530 may obtain an image for inspecting a defect of the inspection target W. In some embodiments, the first detector 530 may include a time delayed integration (TDI) camera or a charge coupled device (CCD) camera. The image for the inspection the defect may be detected in a state where the SNR is improved, and inspection algorithm may be performed on the image to determine whether the defect exists or not. The second detector 540 may be a detector for reviewing the inspection target W. The second detector 540 may be used for a small pattern and accurate alignment. The second detector 540 may be used to review the inspection target W after inspecting the defect.

Additionally, the detection optical unit 500 may further include a second spatial filter array 550. The second spatial filter array 550 may have the same or similar shape and function as the first spatial filter array 150, and thus the detailed descriptions thereto will be omitted. The first and second spatial filter arrays 150 and 550 may have spatial filters having the same opening when the same inspection process is performed. A transmission region of the reflective light L2 corresponding the incident light L1 transmitted through the modified transmission region may be modified by the second spatial filter array 550, and thus, the inspection reliability may be improved. Furthermore, the detection optical unit 500 may further include other optical device located on the optical path. For example, the detection optical unit 500 may further include a polarizing filter disposed in front of the second spatial filter array 550.

The control unit 600 may control the illumination optical unit 100, the inspection target unit 200, the objective lens unit 300, the first beam splitter 400, and the detection optical unit 500. As described above, the control unit 600 may control the optical inspection apparatus 10 to design the opening of the processing filter 154 using the reference filter 152. The control unit 600 may compare and analyze the defect data according to the position of the reference hole 152a to extract the excess regions in which the SNR is higher than the critical value. The control unit 600 may set the design region DR of the opening based on the excess regions.

The control unit 600 may perform the defect inspection process on the inspection target W on which a treating process is performed. For example, the treating process may be a process which is necessary to manufacture a semiconductor device on the inspection target W (e.g., a semiconductor wafer). The control unit 600 may select the processing filter optimized according to a type of a defect, a type of a recipe, a type of the inspection target W, and/or a material of the inspection target W and may then perform the inspection process using the selected processing filter. For example, the control unit 600 may perform an inspection process, which inspects a first defect using a first processing filter having a first opening, on a first substrate on which a first process is performed. In addition, the control unit 600 may perform an inspection process, which inspects a second defect using a second processing filter having a second opening, on a second substrate on which a second process is performed. Here, the first substrate may be the same as the second substrate, the first process may be the same as the second process, or the first defect may be the same as the second defect. In some embodiments, when a single inspection process is performed, the control unit 600 may select a plurality of processing filters and may perform the single inspection process using the plurality of selected processing filters. For example, the control unit 600 may perform an inspection process using a first processing filter having a first opening and a second processing filter having a second opening when the inspection process is performed on a first substrate on which a first process is performed. In some embodiments, the control unit 600 may repeatedly perform the scanning process of designing the opening using the reference filter 152 a plurality of times and may extract average data of obtained data to design the opening.

The control unit 600 may control the protective fluid supply part 330a or 330b to supply the protective fluid to the objective lens 310. In particular, the control unit 600 may control the protective fluid supply part 330a or 330b to supply the protective fluid to the bottom surface 310a of the objective lens 310. The control unit 600 may select one, optimized to a corresponding magnification, of the first to third tube lenses 514a to 514c having the magnifications different from each other. Since the image is obtained using the selected tube lens having the minimum aberration at the corresponding magnification, the quality of the image may be improved. In addition, the control unit 600 may process the image signals obtained from the first and second detectors 530 and 540 to generate image data and may include a display part (not shown) displaying the image data.

Even though not shown in the drawings, the optical inspection apparatus 10 may further include a relay part (not shown) disposed on the optical path. Spatial limitation may be reduced or minimized by the relay part, and thus the optical path may be set freely. In addition, various kinds of optics may be further provided on the optical path, and sensors (not shown) may be provided to sense the optics, respectively. For example, a monitoring sensor part (not shown) may be provided to sense the first and second spatial filter arrays 150 and 550.

According to some embodiments of the inventive concepts, the spatial filter may be designed to have the opening optimized according to a type of the substrate on which the optical inspection process is performed, a type of the recipe of the treating process performed on the substrate, and/or a type of the defect to be detected from the substrate. The hole restricting the irradiation region may be disposed on the optical path of the incident light, and then the scanning process may be performed while moving the hole. Thus, the defect data according to the position of the hole may be obtained. The defect data may be compared and analyzed to extract the excess regions in which the SNR is higher than the critical value. The opening of the spatial filter may be designed based on the positions of the excess regions. In addition, the tube lens meeting the corresponding magnification may be selected from the plurality of tube lenses when receiving the reflective light, and thus, the aberration may be minimized. Furthermore, the protective fluid may be supplied to the bottom surface of the objective lens to protect the objective lens.

While the inventive concepts have been described with reference to example embodiments, it will be apparent to those skilled in the art that various changes and modifications may be made without departing from the spirits and scopes of the inventive concepts. Therefore, it should be understood that the above embodiments are not limiting, but illustrative. Thus, the scopes of the inventive concepts are to be determined by the broadest permissible interpretation of the following claims and their equivalents, and shall not be restricted or limited by the foregoing description.

What is claimed is:

1. An optical inspection apparatus comprising:
    an inspection target unit on which an inspection target is loaded;
    an illumination optical unit configured to irradiate incident light to the inspection target;
    an objective lens unit disposed between the illumination optical unit and the inspection target unit;
    a detection optical unit receiving reflective light reflected from the inspection target to thereby detect a defect on the inspection target; and
    a control unit connected to the illumination optical unit and the detection optical unit,
    wherein the illumination optical unit comprises:
    a light source part generating the incident light; and
    a plurality of spatial filters modifying a transmission region of the incident light,
    wherein the spatial filters comprise:
        a reference filter having a hole to transmit the incident light; and a plurality of processing filters having openings different from the hole wherein the control unit controls the illumination optical unit to provide the incident light to the defect through the hole using a reference filter and to move the hole relative to the objective lens unit and selects a measurable one of the openings corresponding to an area measured by the hole, and wherein the control unit controls the illumination optical unit to load one of the processing filters having the selected measurable opening between the light source part and the objective lens unit.

2. The optical inspection apparatus of claim 1, wherein the illumination optical unit further comprises a filter movement part including:
a first filter movement part configured to move the spatial filter part in a first direction; and
a second filter movement part configured to move the spatial filter part in a second direction perpendicular to the first direction.

3. The optical inspection apparatus of claim 1, wherein the hole is smaller than the openings.

4. An optical inspection apparatus comprising:
an inspection target unit on which an inspection target is loaded;
an illumination optical unit irradiating incident light to the inspection target;
an objective lens unit disposed between the illumination optical unit and the inspection target unit;
a detection optical unit receiving reflective light reflected from the inspection target to thereby detect a defect on the inspection target; and
a control unit connected to the illumination optical unit and the detection optical unit,
wherein the illumination optical unit comprises:
a light source part generating the incident light; and
a spatial filters modifying a transmission region of the incident light,
wherein the spatial filters comprises:
a reference filter having a hole to transmit the incident light; and
a processing filter having an opening different from the hole
wherein the reference filter comprises:
a light shielding portion; and
a hole surrounded by the light shielding portion,
wherein the control unit designs the opening using a result of a scanning process performed while moving the hole in at least one of the first direction or the second direction,
wherein the control unit obtains defect data while performing the scanning process using the hole when the incident light is irradiated,
wherein the control unit controls the illumination optical unit to move the hole corresponding to excess regions in which a signal-to-noise ratio of the defect data is higher than a critical value previously determined, and
wherein the control unit obtains a shape of the opening designed based on positions of the hole.

5. The optical inspection apparatus of claim 4, wherein the scanning process is performed a plurality of times and wherein the opening is designed using an average value extracted from positions of the hole of the scanning processes performed the plurality of times.

6. The optical inspection apparatus of claim 4, wherein the optical inspection apparatus is a bright field optical system.

7. The optical inspection apparatus of claim 6, wherein the detection optical unit comprises: a tube lens array,
wherein the tube lens array comprises:
a first tube lens having a first magnification; and
a second tube lens having a second magnification.

8. The optical inspection apparatus of claim 7, wherein the first magnification is lower than the second magnification,
wherein the first tube lens is configured to align the inspection target, and
wherein the second tube lens is configured to detect the defect on the inspection target.

9. The optical inspection apparatus of claim 8, wherein the detection optical unit further comprises: a second spatial filter disposed between the tube lens array and the objective lens unit, and
wherein the second spatial filter has a second opening having the same shape as the opening of the processing filter.

10. The optical inspection apparatus of claim 1, wherein the objective lens unit comprises:
an objective lens; and
a protective fluid supply part that supplies a protective fluid to a space between the objective lens and the inspection target.

11. The optical inspection apparatus of claim 10, wherein the protective fluid supply part is disposed outside the objective lens.

12. The optical inspection apparatus of claim 11, wherein the objective lens unit further comprises: an objective lens cover surrounding the objective lens, and
wherein the protective fluid supply part is disposed to penetrate the objective lens cover.

13. The optical inspection apparatus of claim 10, wherein the protective fluid supply part is disposed in a body of the objective lens.

14. An optical inspection apparatus comprising:
an inspection target unit on which an inspection target is loaded;
an illumination optical unit irradiating incident light to the inspection target;
an objective lens unit disposed between the illumination optical unit and the inspection target unit;
a control unit connected to control the illumination optical unit
wherein the illumination optical unit comprises:
a light source part generating the incident light; and
spatial filters modifying a transmission region of the incident light
wherein the spatial filters comprise:
a reference filter having a hole to transmit the incident light; and
a plurality of processing filters having openings different from the hole,
wherein the control unit controls the illumination optical unit to provide the incident light to the defect through the hole using a reference filter and to move the hole relative to the objective lens unit and selects a measurable one of the openings corresponding to an area measured by the hole, and
wherein the control unit controls the illumination optical unit to load one of the processing filters having the selected measurable opening between the light source part and the objective lens unit.

15. The illumination optical system of claim 14, wherein the illumination optical unit further comprises a filter movement part including:

a first filter movement part configured to move the spatial filter part in a first direction; and
a second filter movement part configured to move the spatial filter part in a second direction perpendicular to the first direction.

16. The illumination optical system of claim 14, wherein the hole is smaller than the openings.

17. The illumination optical system of claim 14, wherein the reference filter comprises a plurality of reference filters.

* * * * *